US006928321B1

(12) United States Patent
Kroll

(10) Patent No.: US 6,928,321 B1
(45) Date of Patent: Aug. 9, 2005

(54) HYPNOSIS AUGMENTED ICD

(75) Inventor: Mark W. Kroll, Simi Valley, CA (US)

(73) Assignee: Pacesetter, Inc., Sylmar, CA (US)

(*) Notice: Subject to any disclaimer, the term of this patent is extended or adjusted under 35 U.S.C. 154(b) by 379 days.

(21) Appl. No.: 10/293,800

(22) Filed: Nov. 12, 2002

Related U.S. Application Data

(60) Provisional application No. 60/357,352, filed on Feb. 15, 2002.

(51) Int. Cl.⁷ .............................................. A61N 1/365
(52) U.S. Cl. ....................................................... 607/5
(58) Field of Search .............................. 607/4, 5, 9, 14, 607/15, 30, 32

(56) References Cited

U.S. PATENT DOCUMENTS

| | | | | |
|---|---|---|---|---|
| 4,210,149 A | * | 7/1980 | Heilman et al. ................ | 607/5 |
| 5,332,400 A | * | 7/1994 | Alferness ........................ | 607/5 |
| 5,662,689 A | | 9/1997 | Elsberry et al. ................ | 607/5 |
| 5,792,187 A | | 8/1998 | Adams ............................ | 607/5 |
| 5,817,131 A | | 10/1998 | Elsberry et al. ................ | 607/5 |
| 5,893,881 A | | 4/1999 | Elsberry et al. ................ | 607/5 |
| 6,349,233 B1 | | 2/2002 | Adams ............................ | 607/5 |

FOREIGN PATENT DOCUMENTS

WO    WO 97/09088    3/1997    ............ A61N 1/39

OTHER PUBLICATIONS

Holroyd, J., "Hypnosis Treatment of Clinical Pain: Understanding Why Hypnosis is Useful,"*Int'l Journal of Clinical and Experimental Hypnosis*, vol. XLIV, No. 1, Jan. 1996 331-51.

Eimer, B., "Clinical Applications of Hypnosis for Brief and Efficient Pain Management Psychotherapy,"*American Journal of Clinical Hypnosis*, 43:Jul. 1, 2000.

Baker, G.W. et al., Abstract of "Electroencephalographic Indices Related to Hypnosis and Amnesia During Propofol Anesthesia for Cardioversion", *Anaeth. Intensivie Care 2000* Aug.; 28 (4):386-91.

Deltito, J., "Hypnosis in the Treatment of Acute Pain in the Emergency Department Setting,"*Postgraduate Medical Journal* (Apr. 1984) 60. 263-266.

Nickelson, C. et al. "What If Your Patient Prefers an Alternative Pain Control Method? Self-Hypnosis in the Control of Pain"*Southern Medical Journal*, May 1999, vol. 92, No. 5.

(Continued)

Primary Examiner—George Manuel

(57) ABSTRACT

A system and method for employing hypnosis and other pain self-management techniques to mitigate pain experienced by patients receiving therapeutic ICD shocks. In one aspect, a patient is screened for hypnotic inducibility and provided with at least one of redirection/suggestion training, training in self-hypnosis and hypnotic inducement and direct suggestions for pain mitigation. In other aspects, an implantable stimulation device monitors the patient for an arrhythmic event and provides an indication that a therapeutic shock is impending. The patient can then initiate a pain management technique prior to delivery of the shock. Indications can include an audible tone that can help induce a hypnotic state, a tactile vibration, and/or an electrical stimulation. In certain aspects, delivery of the shock is delayed until the device determines that the patient has achieved an effective pain self-management state, which can include implantee activation of certain therapies.

28 Claims, 4 Drawing Sheets

OTHER PUBLICATIONS

Ouellette, E. "Pain Management and Medical Hypnosis,"*AAOS Instructional Course Lestures*, vol. 49, 2000.

Buchser, E. et al. "Hypnosis and Self-Hypnosis, Administered and Taught by Nurses, for the Reduction of Chronic Pain: A Controlled Clinical Trial,"*Schweiz Med Wochenschr* 1994; 124 (Suppl. 62): 77-81.

Chaves, J.F. "Recent Advances in the Application of Hypnosis to Pain Management,"*Amer J Clin Hypn* 37:2, Oct. 1994.

Logue, P. et al. "Hypnosis Fact or Fiction for Treating Pain and Related Disorders?"*NCMJ* May/Jun. 1998, vol. 59, No. 3.

* cited by examiner

HYPNOSIS AUGMENTED ICD

RELATED APPLICATIONS

This application claims the benefit of U.S. Provisional Application Ser. No. 60/357,352, filed Feb. 15, 2002.

FIELD OF THE INVENTION

The invention relates to the field of implantable medical devices and, in particular, to an implantable cardioverter-defibrillator (ICD) with provision for assisting an implantee enter into a hypnotic state to reduce the sensation of pain from any delivered shocks.

BACKGROUND OF THE INVENTION

ICDs are implantable devices adapted to automatically detect and interrupt rapid, irregular atrial and/or ventricular heart muscle contractions. ICDs typically deliver a high energy and voltage electrical shock to the heart upon detection of an arrhythmic event, such as fibrillation, to override the electrochemical conduction and enable the heart to resume normal rhythm. However, the high energy and voltage shocks delivered by ICDs can cause significant pain to the patient and pain control remains a major issue in ICD therapy.

The pain felt by the patient upon delivery of a shock from the ICD causes moderate to severe physical and psychological trauma. Atrial fibrillation reduces cardiac efficiency, but is not generally lethal, at least on a short term basis. Pain is a major issue limiting the success of high voltage atrial fibrillation (AF) therapies in the patients that are unwilling to tolerate pain for something that was not immediately lethal. Thus, it would be very attractive to have additional techniques to deal with pain for atrial fibrillation.

An additional problem that is often not recognized is how serious the pain issue is for patients with ventricular arrhythmias which can be immediately lethal unless terminated. Even though many patients have no viable alternative other than to accept the pain because the alternative is death, the pain issue causes many patients significant physical and emotional distress.

The pain of the shocks is generally due to two sources: First, inappropriate shocks resulting from a misdiagnosis of or for non-sustained lethal arrhythmias. A misdiagnosis occurs when the device incorrectly detects an arrhythmia and delivers a shock when the patient is not in fact experiencing an arrhythmia that would indicate a shock. A non-sustained arrhythmia in this context is an arrhythmia that self-terminates and can result in inducing the device to appropriately prepare a shock and inappropriately deliver the shock even though the potentially lethal arrhythmia has terminated. In these cases, the patient may be fully conscious to feel the full pain of an inappropriate shock.

The second problem is that rapidly charging devices can deliver the shock while the patient is still conscious in about one third of all cases. This is advantageous as it can eliminate some sequelae due to car accidents, falls, etc., but the patient is conscious so as to feel the full pain of the shock.

The use of rounded waveforms can reduce the pain of the shock as can possible nerve stimulus blocking. However, neither of these measures alone or even in conjunction is generally adequate to eliminate the shock pain or even make it completely tolerable.

Hypnosis has long been used for the control of mild to severe pain. In fact, before the discovery of ether and chloroform in the 1840s, it was one of the few methods available for surgical anesthesia. Careful studies have shown that hypnotizable subjects can reduce pain perception by 3 to 4 points on the classic 10-point pain scale. This is a significant reduction even greater than what would be expected with the use of rounded shock waveforms, for example. Different people have different levels of hypnotic inducibility. It is found that at least 80% of psychologically normal patients are at least somewhat hypnotically inducible. Even those patients that would not be considered clinically inducible can benefit from hypnotic pain reduction. Hypnotic pain reduction is a demonstrable physiological occurrence and can be observed by reduced brainwave response to painful stimuli.

From the foregoing, it will be understood that there is an ongoing need for a system that alleviates a patient's sensation of pain under ICD shocks for both atrial and ventricular arrhythmia treatments. There is a further need to provide this alleviation while maintaining the capability, where possible through rapid charging, to deliver shocks as rapidly as possible to avoid sequelae that may occur if a delay in shocking would lead to unconsciousness.

SUMMARY

The aforementioned needs are satisfied by the invention which, in certain embodiments, is a process of delivering therapeutic electrical stimulation to a patient from an implantable medical device, the process comprising conditioning the patient in a pain management technique, monitoring the patient with the implantable medical device to detect an event indicating delivery of therapeutic electrical stimulation, signaling the patient that a therapeutic electrical stimulation is to be delivered upon detection of the event to thereby allow the patient to implement the pain management technique, and delivering the therapeutic electrical stimulation after the patient has initiated the pain management technique.

In one illustrative embodiment, conditioning the patient in a pain management technique can comprise implanting a hypnotic suggestion in the mind of the patient such that the patient, upon receiving the signal from the implantable medical device, enters a hypnotic state such that the perception of pain by the patient is reduced when the therapeutic electrical stimulation is provided to the patient. Alternatively or in addition, conditioning the patient in a pain management technique can comprise training the patient to self-hypnotize upon receiving the signal.

Another embodiment is a method of delivering therapeutic stimulation to patients provided with implantable cardiac stimulation devices, the method comprising evaluating the patient to determine a hypnotic inducibility score, performing at least one of the following in accordance with the determined inducibility score of the patient: 1) inducing hypnosis and providing a direct suggestion to self-manage pain; 2) training the patient to self-hypnotize; and 3) attempting hypnotic induction and teaching the patient redirection and suggestion techniques, monitoring the patient to detect an arrhythmic condition indicating delivery of a therapeutic shock, notifying the patient upon detection of the arrhythmic condition, confirming indication of delivery of a therapeutic shock, and delivering a therapeutic shock. Delivering the therapeutic shock can be delayed a determined period after detection of an arrhythmic condition.

Yet another illustrative embodiment is an implantable therapeutic cardiac device comprising at least one implantable sensor, a stimulation circuit adapted to provide therapeutic electrical stimulation, a controller in communication with the at least one implantable sensor and the stimulation circuit such that upon detection of a cardiac arrhythmia as sensed by the at least one implantable sensor, the controller can induce the stimulation circuit to provide a therapeutic stimulation, and an annuciator in communication with the controller and adapted to notify a patient when the device has detected an arrhythmia indicating delivery of a therapeutic stimulation.

DETAILED DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
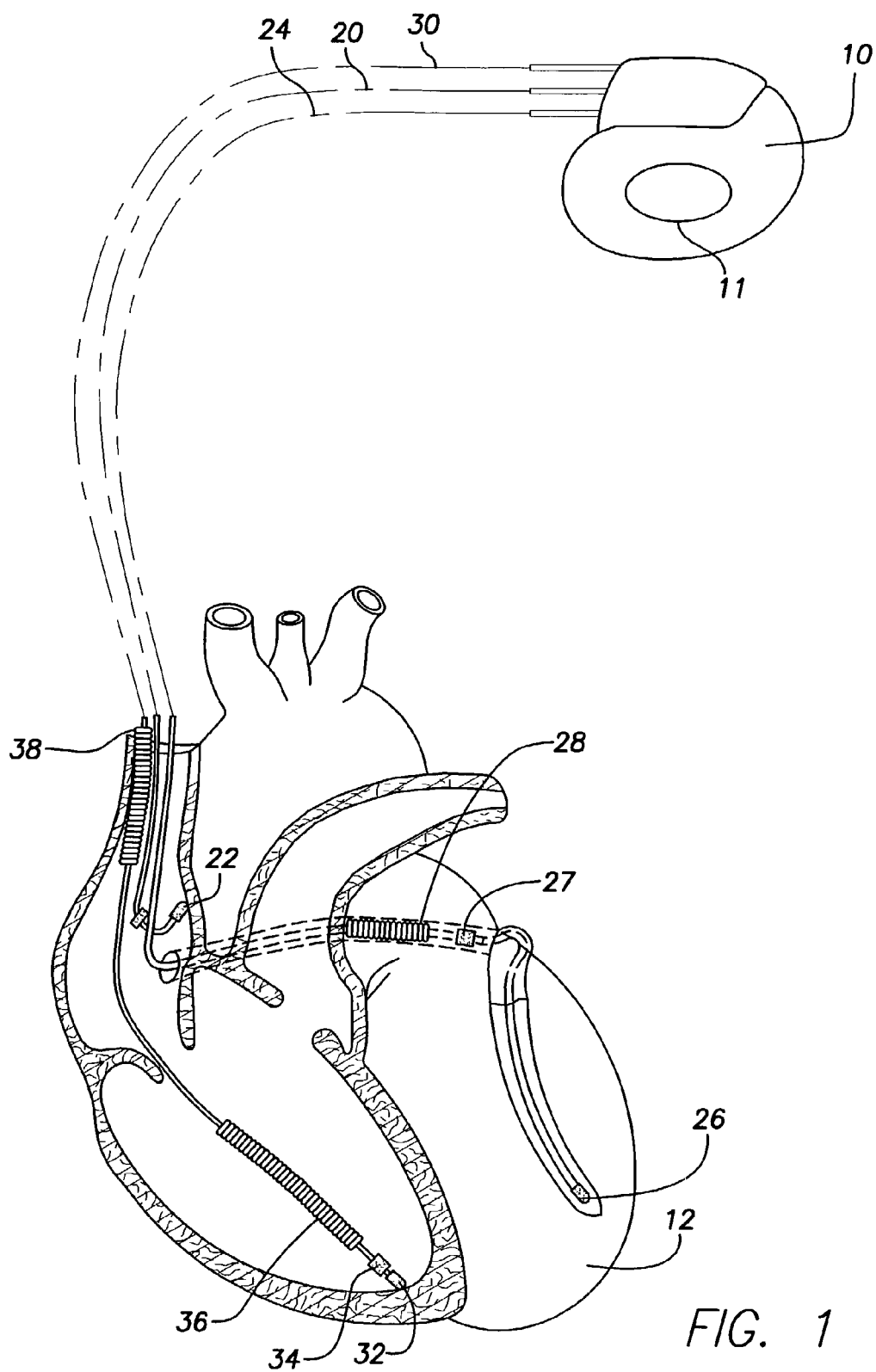
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device augmented with hypnosis 10, referred to hereafter as "device 10" for brevity, in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

In this embodiment, the device 10 also includes an annuciator 11. In one embodiment, the annuciator 11 comprises a speaker that provides physical vibrations that can be discerned by the patient either as audible sounds and/or as a tactile sensation. In other embodiments, the annuciator 11 comprises a relatively low voltage electrical stimulator that provides discernable, but non-painful distinctive electrical stimulation to the patient. The output of the annuciator 11 serves to notify the patient when the device 10 has determined that an arrhythmic condition is present and that a potentially painful shock is indicated and will follow shortly. With the notification thus provided by the device 10, the patient can initiate a pain management technique such as will be described in greater detail below with reference to FIGS. 3 and 4.

In this embodiment, the annuciator 11 is shown as comprised within the device 10, however, in alternative embodiments, a annuciator 11 can be provided as part of an implantable device that can be implanted in another location to facilitate notification of the patient. In other alternative embodiments, the annuciator 11 can be included as a non-implantable device, such as with a bedside monitor or a device worn on the wrist or belt.

Figure 2:
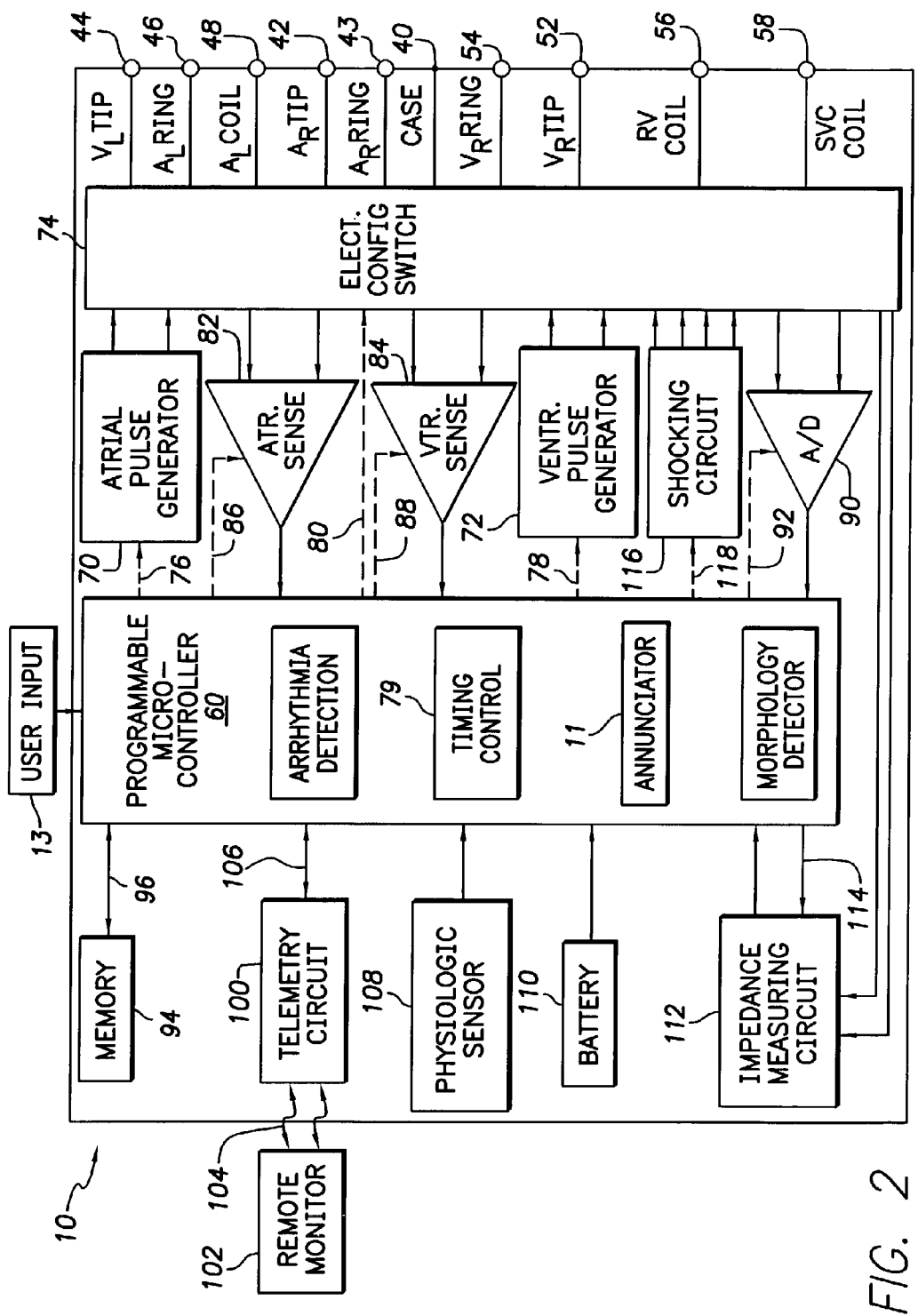
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate, or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller (CPU) 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart 12, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, post-ventricular atrial refractory period (PVARP) intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart 12. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart 12. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an event which may be an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102, such as a remote monitor for example. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart 12 is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via a control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

As previously described, the memory 94 can also store sensed data relating to cardiac activity. A feature of the present invention is the ability to sense and store a relatively large amount of data (e.g., from the data acquisition system 90), which data may then be used for subsequent analysis to guide the programming of the device 10. A further feature of the invention is to automatically manage the operation of the device 10 to improve the efficiency of storage of sensed data as well as device 10 programming as will be described in greater detail below.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart 12, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. The type of sensor used is not critical to the present invention and is shown only for completeness.

The stimulation device additionally includes a battery 110 which provides operating power to all of the circuits shown in FIG. 2. For the stimulation device 10, which employs shocking therapy, the battery 110 must be capable of operating at low current drains for long periods of time (preferably less than 10 $\mu$A), and then be capable of providing high-current pulses (for capacitor charging) when the patient requires a shock pulse (preferably, in excess of 2 A, at voltages above 2 V, for periods of 10 seconds or more). The battery 110 must also have a predictable discharge characteristic so that elective replacement time can be detected.

As further shown in FIG. 2, the device 10 is shown as having an impedance measuring circuit 112 which is enabled by the microcontroller 60 via a control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart 12 aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode 36 as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In certain embodiments, the device 10 further comprises a user input 13. The user input 13 is in communication with the microcontroller 60 so as to allow a user, such as for example an implantee provided with the device 10, to provide control inputs to the microcontroller 60 so as to affect device 10 operation. In one embodiment, the user input 13 allows a user to provide a control input to the microcontroller 60 following a signal from the annuciator 11 that a therapeutic stimulation from the device 10 is indicated. The control input provided to the device 10 via the user input 13 can indicate that the user has received notification of the indicated therapeutic stimulation, has initiated an appropriate pain management technique, and that the user is ready to receive the therapeutic stimulation. The user input 13 can be in direct communication with the microcontroller 60 as shown in FIG. 2 or can be in indirect communication, such as via the telemetry circuit 100.

Figure 3:
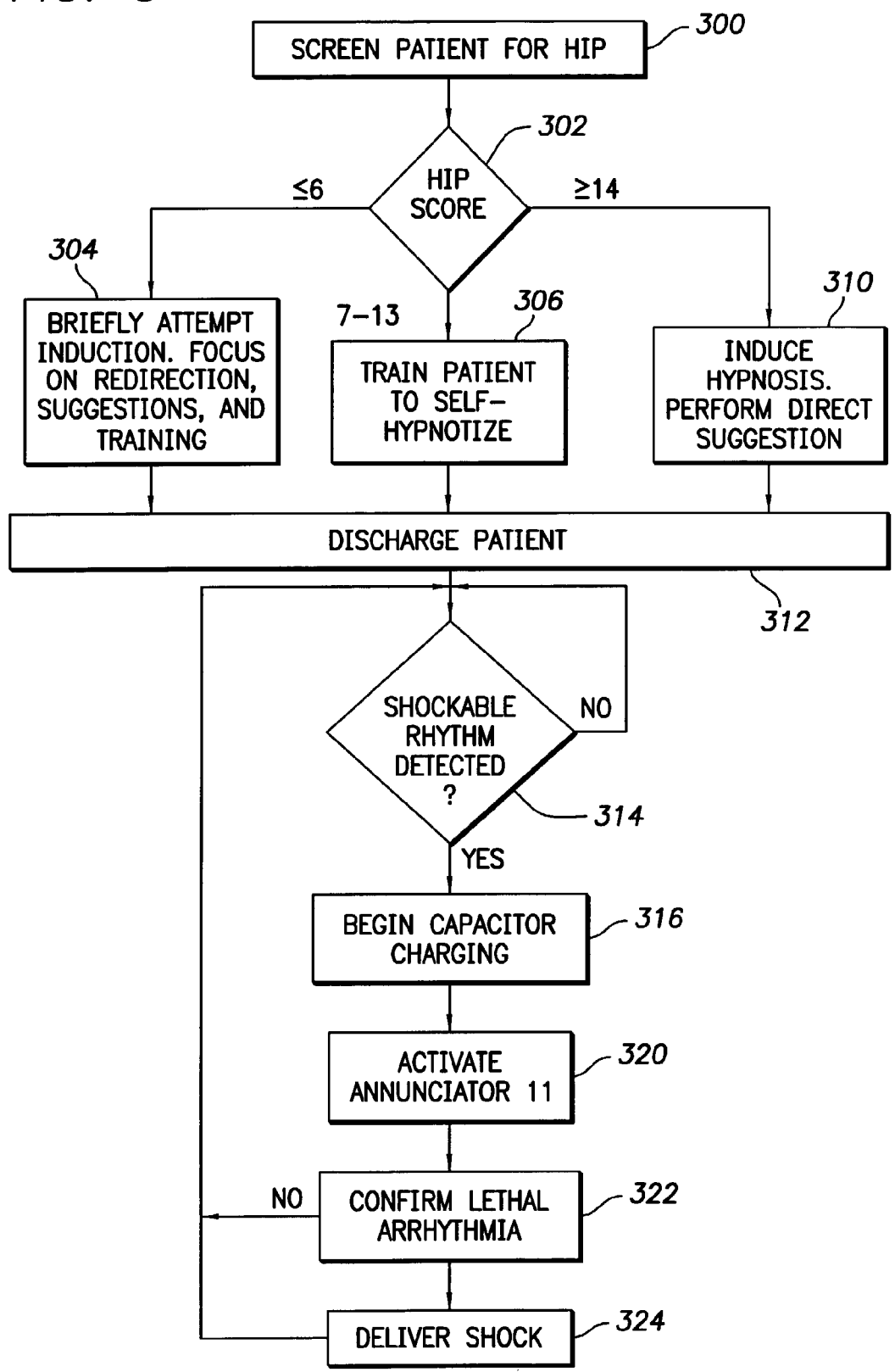
FIG. 3 is a flow chart describing a high level overview of a method of using an implantable device augmented with hypnosis to reduce patient pain perception.
Figure 4:
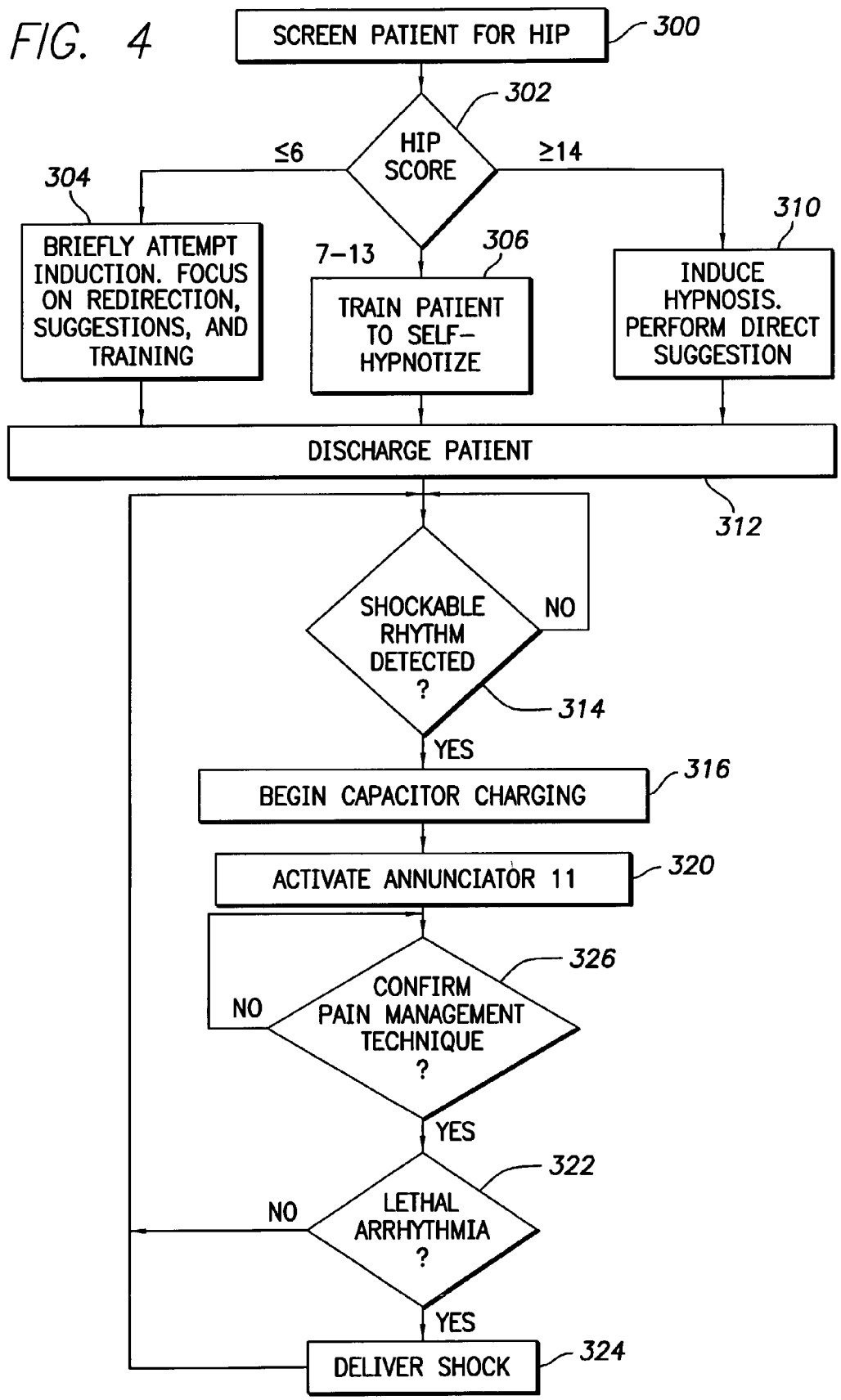
FIG. 4 is a flow chart of an alternative embodiment of the basic method show in FIG. 3.

In FIGS. 3 and 4, flow charts are shown describing overviews of the operation and novel features implemented in embodiments of the device 10. It should be understood that the actions performed as indicated in FIGS. 3 and 4 and described in greater detail below are partially performed by the implantable device 10. In these flow charts, the various algorithmic steps are summarized in individual "blocks". Such blocks describe specific actions or decisions that are made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

To begin with, the patient is screened for hypnotic inducibility in step 300. This results in a hypnotic inducibility score called the "Hypnotic Induction Profile." The HIP indicates the patient's motivation and willingness to comply with the clinician's directives and suggestions as part of the hypnotic induction ritual. It also assesses the patient's capacity to experience hypnotic phenomena relative to inducing hypnotic analgesia. These phenomena include speed and authenticity of responsiveness to hypnotic suggestions; imagination capability; and the ability to: enter a relaxed state; suspend voluntary control; experience an altered state of consciousness; feel a floating sensation; produce a signaled arm levitation; perceive physical disassociations; respond to post-hypnotic suggestions; and experience spontaneous amnesia.

A HIP can generally be determined within ten minutes by a practitioner of ordinary skill. The HIP is a numeric score indicating the inducibility of the patient with larger scores indicating a greater inducibility.

Once the HIP is determined, a decision is made in step 302 according to the patient's HIP score. If the HIP is greater than or equal to 14, then the patient is considered highly hypnotizable and direct suggestion will generally be effective for blocking the pain of delivered shocks. In step 304, the patient is then induced into hypnosis. A direct suggestion will be given. An example suggestion would be "When you hear the tone, you will then experience a mild tingling in your chest. This tingling is good for you and will not hurt."

If the patient has a intermediate HIP score of, in this embodiment, 7–13, then the practitioner will train the patient to self-hypnotize in step 306. Each patient will then be instructed to self-hypnotize when they perceive the notification, such as pleasant sounds, from the annuciator 11 warning of an impending shock. As previously described the annuciator 11 may be embodied within the device 10, but can also be embodied solely in and/or be augmented by a remote hip worn speaker, wrist watch worn device, or a bedside monitor.

For patients with a low HIP score ($\leq 6$ in this embodiment), the practitioner will briefly attempt induction in step 310. If the induction is not satisfactory, then the practitioner will focus on redirection suggestions and training. The patient will be instructed on how to relax when the alert is given. Redirection strategies can include having the patient visualize that the stimulation is coming from another part of the body such as, for example, the foot, to distract them from the strong sensation in the chest.

It will be understood by one of ordinary skill in the art that there are a variety of known methodologies and approaches to inducing hypnosis and providing suggestions. The exact methods of inducing or attempting to induce hypnosis or the exact suggestions or redirection training provided as previously described are not crucial to the invention. It is intended to be within the scope of the invention to include a variety of specific hypnotizing techniques well known in the art and the variety of specific techniques will not be described in greater detail here.

Following the screening of step 300 and the training of step 304, 306, or 310, the patient is then discharged home in step 312. The device 10 then monitors the heart 12 on an ongoing manner for detection of a possible arrhythmia indicating delivery of a shock in step 314. If such an arrhythmia is detected, then the device 10 will begin capacitor charging in step 316. Substantially simultaneously, in step 320, the device 10 will activate the annuciator 11 which, in certain embodiments, begins to emit a pleasant, distinctive sound. The annunciation will generally lead the highly inducible patient (HIP$\geq$14) directly into the direct suggestion so they will literally feel little to no pain. The annunciation will help a moderately hypnotizable ($7 \leq HIP \leq 13$) trained patient to self-hypnotize and significantly reduce their sensation of the pain of a shock delivery. The annunciation will also, in many cases, help the low hypnotizable patient (HIP$\leq$6) to begin relaxation and redirection thinking.

The device 10 then evaluates the arrhythmia to confirm continued indication of shock delivery in step 322. If the device 10 determines that a shock is no longer indicated, the device 10 will then generally discharge the capacitors in one of a variety of manners known in the art and return to the ongoing monitoring of state 314. If the device 10 determines that delivery of a shock is indicated, it will then do so in step 324 and return to the monitoring of state 314.

FIG. 4 is a flow chart of an alternative embodiment of a stimulation device augmented with hypnosis 10. The operation of the device 10 in this embodiment is substantially similar to that previously described with respect to FIG. 3 and the same reference numbers will indicate substantially identical processes, however with the addition of an additional decision state 326. In particular, the decision state 326 comprises a confirmation of the utilization of a pain management technique.

In certain embodiments, the decision of state 326 occurs passively from the perspective of the patient. For example, the device 10 may introduce an intentional delay between the onset of capacitor charging of step 316 and activation of the annuciator in state 320 until the delivery of the shock in state 324 under the assumption that the delay provides the patient time to undertake appropriate pain management techniques. The delay may be a programmable aspect of the device 10 operation. For example, a physician may program a delay determined by an average or minimum time for a particular patient to initiate their particular pain management technique(s).

The device 10 may also actively monitor one or more patient physiological measured parameters and evaluate these monitored parameters to determine whether the pain management technique(s) have been engaged. For example, in certain embodiments, the physiological sensor(s) 108 of the device 10 are adapted to determine a transthoracic impedance. This physiological measurement can determine the rate and depth of the patient's breathing. A deepening of respiration tidal volume and a generally corresponding reduction in respiration rate is indicative of a focused state of relaxation that corresponds to achievement of a hypnotic state or other pain management technique diverting the patient's attention from pain of a potential shock. Upon observation that this deepening and slowing of breathing has occurred, the device 10 would then return a positive result of the decision of state 326. Determined values or ranges for a change in respiration rate and/or depth or other physiological parameters may also be programmable aspects of the device 10 operation.

In yet other alternative embodiments, the determination of state 326 can include active input from the patient for non-lethal arrhythmias. For example, the device 10 can include provision for patient input via the input device 13 and a positive decision result of state 326 can comprise patient activation of the input device 13 indicating sufficient engagement of a pain management technique. In this case, the method is modified so that, once the patient has achieved a hypnotic or relaxed state, the shock is discharged voluntarily.

It will be understood that in the previously described embodiments, delivery of the shock in state 324 would not be delayed beyond a safe time delay in case of potentially lethal arrhythmias, such as ventricular arrhythmias. Thus, in cases of potentially lethal arrhythmias, the device 10 would deliver a shock as indicated in state 324 whether or not a positive decision has been returned by state 326.

Another aspect of the invention is to have the annunciator 11, such as tone generator, embodied in and generated by a remote home monitor. In this embodiment, the device 10 would signal the remote monitor, such as via the telemetry circuit 100, that a shock was needed. After confirming that the patient was in acoustical range (for an atrial shock) the remote monitor would deliver the annunciation, such as for example, hypnotic tones or speech and signal the device 10 that it could deliver the shock. In the case of a ventricular fibrillation, the monitor would still attempt the hypnosis but the device 10 would not wait for the confirmation to deliver the shock.

A variant on this embodiment would have a patient activator give the annunciation, such as hypnotic tones or verbal suggestion. When the patient wished to have an AF shock, they would then actuate the user input 13, such as pushing the appropriate button on the activator. The activator would then begin delivering the hypnotic tones or speech while the device 10 was charging its capacitors and waiting for the hypnosis to occur. A second stage could be added to this embodiment in which the patient would be instructed to provide a subsequent user input, such as pushing a second button after the trance had occurred or they were deep enough into hypnosis.

Although the preferred embodiments of the present invention have shown, described and pointed out the fundamental novel features of the invention as applied to those embodiments, it will be understood that various omissions, substitutions and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. A method of delivering therapeutic electrical stimulation to a patient from an implantable medical device, the method comprising:
   conditioning the patient in a pain management technique;
   monitoring the patient with the implantable medical device to detect an event indicating delivery of therapeutic electrical stimulation;
   signaling the patient that a therapeutic electrical stimulation is to be delivered upon detection of the event; and
   delivering the therapeutic electrical stimulation after signaling the patient;
   wherein conditioning the patient in a pain management technique comprises at least one of implanting a hypnotic suggestion in the mind of the patient such that the patient, upon receiving the signal from the implantable medical device, enters a hypnotic state and training the patient to self-hypnotize upon receiving the signal.

2. The method of claim 1, wherein conditioning the patient in a pain management technique comprises training the patient to self-hypnotize upon receiving the signal.

3. The method of claim 1, wherein signaling the patient comprises delivering a discernable electrical stimulation to the patient from the implantable medical device.

4. The method of claim 1, wherein signaling the patient comprises activating an annunciator to provide a perceptible signal to the patient.

5. The method of claim 1, further comprising sensing whether the patient has initiated the pain management technique.

6. The method of claim 5, wherein delivering the therapeutic electrical stimulation occurs in response to sensing that the patient has initiated the pain management technique.

7. The method of claim 5, wherein sensing whether the patient has initiated the pain management technique comprises using a sensor of the implantable medical device to monitor a physiologic parameter of the patient to ascertain whether the physiologic parameter is indicative of the patient having initiated the pain management technique.

8. The method of claim 7, wherein using a sensor of the implantable medical device to monitor a physiologic parameter of the patient comprises monitoring the patient's heart rate.

9. The method of claim 1, wherein delivering the therapeutic electrical stimulation after signaling the patient comprises delivering the therapeutic electrical stimulation a predetermined time delay after detecting an event indicating delivery of therapeutic electrical stimulation.

10. The method of claim 1, wherein delivering the therapeutic electrical stimulation after signaling the patient comprises delivering the therapeutic electrical stimulation following receipt of a user input indicating initiation of the pain management technique.

11. A method of delivering therapeutic electrical stimulation to a patient from an implantable medical device, the method comprising:
   conditioning the patient in a pain management technique;
   monitoring the patient with the implantable medical device to detect an event indicating delivery of therapeutic electrical stimulation;

signaling the patient that a therapeutic electrical stimulation is to be delivered upon detection of the event;

sensing whether the patient has initiated the pain management technique; and delivering the therapeutic electrical stimulation after signaling the patient and sensing that the patient has initiated the pain management technique;

wherein sensing whether the patient has initiated the pain management technique comprises using a sensor of the implantable medical device to monitor a physiologic parameter of the patient to ascertain whether the physiologic parameter is indicative of the patient having initiated the pain management technique; and wherein using a sensor of the implantable medical device to monitor a physiologic parameter of the patient comprises monitoring at least one of the respiration rate and depth of the patient.

12. The method of claim 11, wherein conditioning the patient in a pain management technique comprises implanting a hypnotic suggestion in the mind of the patient such that the patient, upon receiving the signal from the implantable medical device, enters a hypnotic state.

13. The method of claim 11, wherein ascertaining whether the physiologic parameter is indicative of the patient having initiated the pain management technique comprises detecting at least one of the patients respiration depth increasing beyond a determined baseline and the patients respiration rate decreasing below a determined baseline.

14. The method of claim 11, wherein using a sensor of the implantable medical device to monitor a physiologic parameter of the patient comprises monitoring a transthoracic impedance of the patient.

15. A method of delivering therapeutic stimulation to a patient provided with an implantable cardiac stimulation device, the method comprising:

evaluating the patient to determine a hypnotic inducibility score;

training the patient in a pain management technique in accordance with the determined hypnotic inducibility score of the patient;

monitoring the patient to detect an arrhythmic condition indicating delivery of a therapeutic shock;

notifying the patient upon detection of the arrhythmic condition such that they can undertake the pain management technique; and delivering a therapeutic shock after notifying the patient.

16. The method of claim 15, wherein delivering the therapeutic shock is delayed a determined period after detection of an arrhythmic condition.

17. The method of claim 15, further comprising:

prior to delivering the therapeutic shock, monitoring the patient to determine that a pain management technique has been initiated.

18. The method of claim 17, wherein the delivery of the therapeutic shock is delayed until it is determined that the patient has initiated the pain management technique.

19. The method of claim 17, wherein monitoring the patient to determine that a pain management technique has been initiated comprises confirmation of a user input.

20. The method of claim 17, wherein monitoring the patient comprises monitoring at least one physiological parameter indicative of initiation of a pain management technique.

21. The method of claim 20, wherein monitoring at least one physiological parameter comprises monitoring at least one of the patient's respiration depth, respiration rate, and heart rate.

22. The method of claim 20, wherein the monitoring at least one physiological parameter comprises monitoring at least one of the patient's respiration depth and respiration rate.

23. The method of claim 15, wherein training the patient in a pain management technique comprises performing at least one action selected in accordance with the determined hypnotic inducibility score of the patient, the action being selected from the group consisting of:

inducing hypnosis and providing a direct suggestion to self-manage pain;

training the patient to self-hypnotize; and attempting hypnotic induction and teaching the patient redirection and suggestion techniques.

24. An implantable therapeutic cardiac device comprising:

at least one implantable sensor;

a stimulation circuit adapted to provide therapeutic electrical stimulation;

detection circuitry connected to the at least one implantable sensor, wherein the detection circuitry is operative to detect a cardiac arrhythmia based on signals from the at least one implantable sensor;

a controller in communication with detection circuitry and the stimulation circuit such that upon detection of a cardiac, arrhythmia by the detection circuitry, the controller can induce the stimulation circuit to deliver a therapeutic stimulation; and an annunciator in communication with the controller and adapted to notify a patient when the detection circuitry has detected an arrhythmia, wherein the controller is operative to monitor the at least one implantable sensor to determine that the patient has initiated a pain management technique in response to the notification, and wherein the controller is operative to delay delivery of the therapeutic stimulation until determining that the patient has initiated a pain management technique;

wherein determining that the patient has initiated a pain management technique comprises determining that the patient has entered a hypnotic state.

25. The device of claim 24, further comprising a user input in communication with the controller.

26. The device of claim 25, wherein delivery of the therapeutic stimulation may be delayed until receipt by the controller of a signal from the user input.

27. The device of claim 24, wherein the controller, upon detection of an arrhythmia indicating delivery of a therapeutic stimulation, can induce the stimulation circuit to deliver the therapeutic stimulation after a programmable delay after activation of the annunciator.

28. The device of claim 24, wherein the controller is operative to monitor the at least one implantable sensor to determine that the patient has initiated the pain management technique in response to the notification by detecting at least one of the patient's respiration rate and respiration depth.

* * * * *